United States Patent [19]

Shipchandler

[11] 4,239,772

[45] Dec. 16, 1980

[54] ALLYL AND PROPYL ZEARALENONE DERIVATIVES AND THEIR USE AS GROWTH PROMOTING AGENTS

[75] Inventor: Mohammed T. Shipchandler, Terre Haute, Ind.

[73] Assignee: International Minerals & Chemical Corp., Terre Haute, Ind.

[21] Appl. No.: 43,801

[22] Filed: May 30, 1979

[51] Int. Cl.$^3$ ............... C07D 313/00; A61K 31/365
[52] U.S. Cl. .................... 424/279; 260/343.41
[58] Field of Search .................. 260/343.41; 424/279

[56] References Cited

U.S. PATENT DOCUMENTS

| | | | |
|---|---|---|---|
| 3,196,019 | 7/1965 | Andrews | 260/343.41 |
| 3,239,341 | 3/1966 | Hodge et al. | 260/343.41 |
| 3,239,342 | 3/1966 | Hodge et al. | 260/343.41 |
| 3,239,345 | 3/1966 | Hodge et al. | 260/343.41 |
| 3,239,347 | 3/1966 | Hodge et al. | 260/343.41 |
| 3,239,354 | 3/1966 | Hodge et al. | 260/343.41 |
| 3,239,355 | 3/1966 | Hodge et al. | 260/343.41 |
| 3,373,037 | 3/1968 | Abbott | 260/343.41 |
| 3,373,039 | 3/1968 | Hodge et al. | 260/343.41 |
| 3,915,966 | 10/1975 | Hodge et al. | 544/147 |
| 3,954,805 | 5/1976 | Kavka | 260/343.41 |
| 4,052,414 | 10/1977 | Peters | 260/343.41 |
| 4,088,658 | 5/1978 | Robertson | 260/343.41 |

OTHER PUBLICATIONS

Shipchandler Heterocycles 3, 471 (1975), Peters, J. Med. Chem. 15, 867 (1972).
Bolliger et al. Helv. Chim. Acta, 55, 3030 (1972).
Windholz et al. J. Org. Chem. 15 1647, 1972 Urry et al. Tetrahedron Letters 3109 (1966).

*Primary Examiner*—Henry R. Jiles
*Assistant Examiner*—Jane T. Fan
*Attorney, Agent, or Firm*—Bernard & Brown

[57] ABSTRACT

Resorcylic acid lactone compounds of the formula:

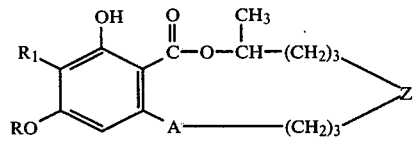

wherein -A- is either $-CH_2-CH_2-$ or $-CH=CH$; >Z is either $>CH_2$, $>C=O$ or $>CH-OH$; and R and $R_1$ are either H or a $C_3$ group selected from propyl and $-CH_2CH=CH_2$, and are different from each other. Such compounds and their derivatives are provided as growth promoting agents for animals, e.g. ruminants and poultry.

7 Claims, No Drawings

ALLYL AND PROPYL ZEARALENONE DERIVATIVES AND THEIR USE AS GROWTH PROMOTING AGENTS

This invention relates to novel, organic compounds having animal growth promoting properties. More particularly, the invention relates to compounds that can be prepared by reacting allyl halides with various resorcylic acid lactone derivatives.

The compounds of the present invention are those of the formula:

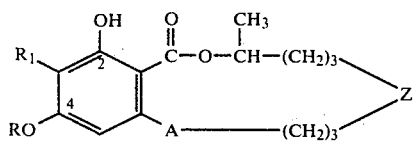

wherein —A— is either —$CH_2$—$CH_2$— or —CH═CH—; >Z is either >$CH_2$, >C═O or >CH—OH; and R and $R_1$ are either H or a $C_3$ group selected from propyl and —$CH_2CH$═$CH_2$, and are different from each other. The hydrogen of the hydroxyl group in the second position of the resorcylic acid lactone part of the molecule can be substituted, for instance with substituted or unsubstituted alkyl, e.g., containing from 1 to about 15 carbon atoms including lower alkyl such as methyl, ethyl, hexyl, etc., and cycloalkyl, particularly monocyclic cycloakyl of about 5 to 8 carbon atoms, such as cyclopentyl, cyclohexyl, methyl cyclohexyl, etc.; alkanoyl, generally containing 1 to about 25 or more carbon atoms including lower alkanoyl such as acetyl, propionyl, valeryl, etc.; substituted or unsubstituted aryl, for instance, monocyclic aryl containing about 6 to 10 carbon atoms or more, such as phenyl, tolyl, etc.; and aryl alkyl (that is an alkyl group having an aryl substituent thereon), wherein the aryl substituent may be monocyclic aryl containing about 6 to 10 carbon atoms or more and the alkyl group is generally lower alkyl, for example, 1 to about 6 carbon atoms, examples of such aryl alkyl compounds including benzyl, bromobenzyl, tolyl methyl, and the like. The preferred compounds herein are the allyl derivatives of zearalenone, i.e., allyl compounds of the above formula wherein —A— is —CH═CH— and >Z is >C═O; and the propyl derivatives of zearalanone, i.e., propyl compounds of the above formula wherein —A— is —$CH_2$—$CH_2$ and >Z is >C═O.

The allyl derivatives of the present invention can be prepared by reacting an allyl halide, e.g., allyl chloride or allyl bromide, with a resorcylic acid lactone, hereinafter referred to as a "zearalin", of the formula:

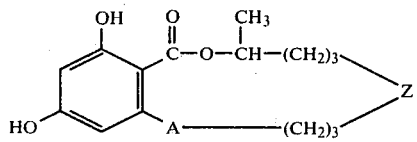

wherein —A—, and >Z, are as defined above. Such a reaction produces a 4-O-allylzearalin which can be converted to the 3-allylzearalin by the Claisen rearrangement reaction. The allyl zearalins can in turn be reduced to the propyl zearalins by low pressure hydrogenation.

The reaction of the allyl halide and zearalin derivative to prepare the allyl compounds herein can generally be effected at about 45° to 80° C., preferably about 50° to 60° C. Preferably the reactants are in solution in solvent-providing amounts of an inert organic solvent containing, for instance, oxygen along with carbon and hydrogen, such as alkanols, e.g., isopropanol, ethanol, methanol; alkyl ethers; aldehydes, ketones, e.g. acetone; etc. The solvent is frequently provided in an amount of about 5 to 25 or more, particularly about 13 to 15, times by weight, of the zearalin. Alkaline catalysts, e.g., $K_2CO_3$, can be employed to facilitate formation of the desired allyl derivative. Reaction time may vary depending upon the particular zearalin employed, temperatures used, etc., but the reaction will often be complete in about 12 hours or less, for instance, about 8 to 10 hours. The ratios of the reactants that can be employed in the reaction mixture are generally about 1 to 5 moles of allyl halide per mole of the zearalin.

Preparation of the 3-allylzearalins involves the Claisen rearrangement of the 4-O-allylzearalins prepared as hereinbefore described. The Claisen rearrangement can be effected by heating the 4-O-allylzearalin in its crystalline form to within a temperature range, e.g. about 185° to 200° C., preferably about 190° to 195° C., and for a period of time, suitable for the Claisen rearrangement to occur. For the preferred allyl zearalenone materials of the present invention, 4-O-allylzearalenone is heated to a temperature of from about 190° to 195° C. for a period of about 5 hours.

When the —A— moiety of the lactone ring is —CH═CH—, both trans- and cis-stereoisomers of the allylzearalins can be prepared. The trans-stereoisomer of the 3-allylzearalin is generally formed in the Claisen rearrangement reaction. This trans- material can be isomerized to the corresponding cis-material using the photoisomerization techniques set forth in Peters, *J. Med. Chem.*, 15, p. 867 (1972), incorporated herein by reference.

The propylzearalins of the present invention can be derived from the allylzearalins by low pressure hydrogenation procedures. Hydrogenation of the allylzearalin is generally carried out at pressures ranging from about 1 to 50 atmospheres and at ambient temperatures, i.e. temperatures from about 15° to 40° C. Advantageously, hydrogenation can be conducted in the presence of a hydrogenation catalyst, e.g., a Group VIII metal, particularly platinum or palladium, on a suitable carrier, e.g. charcoal. Generally the catalyst contains from about 0.01% to about 10% by weight of the catalytic metal. The catalyst can be used in a ratio of from about 0.02 to 2 grams of catalyst, preferably from about 0.1 to 0.5 gram of catalyst, per gram of allylzearalin. Hydrogenation may be carried out while the allylzearalin is dissolved in a suitable solvent, e.g., an alcohol, especially a lower alkanol such as 2-propanol, methanol, ethanol and/or an acid, e.g. acetic acid. When the preferred allylzearalenones are hydrogenated, preferably both the allyl and lactone ring carbon—carbon double bonds are reduced, thereby providing the preferred propylzearalanone materials.

Recovery and refinement of the compounds of the present invention can be by conventional techniques, for example by crystallization, filtration, and recrystallization.

The zearalins employed in making the allyl and propyl derivatives herein can be prepared by known methods. The preferred zearalin for use herein, i.e. zearalenone (—A— is —CH=CH—, and >Z is >C=O), can be obtained by cultivation of the microorganism *Gibberella zeae* (Gordon) in a suitable fermentation medium, as described, for example, in U.S. Pat. No. 3,196,019, incorporated herein by reference.

Zearalenone may conveniently be employed to prepare others of the zearalins which may be used to provide the allyl and propyl compounds herein. For instance, the unsaturated carbon bond in the lactone zearalenone ring can be hydrogenated according to the hydrogenation procedures set forth above and in U.S. Pat. No. 3,239,354. The keto group of zearalenone may be converted to >CHOH by the procedure disclosed in U.S. Pat. No. 3,239,341. The keto group of zearalenone may be converted to >CH$_2$ by a procedure also disclosed in U.S. Pat. No. 3,239,341. Replacement of the hydrogen of the hydroxy groups of the zearalins with an alkyl, alkanoyl, aryl, or aryl alkyl radical is disclosed in U.S. Pat. Nos. 3,239,342, 3,239,347, and the above-mentioned patents.

The allyl and propyl derivatives of the present invention act as growth promoting agents in animals, e.g., ruminants and poultry. The allyl and propyl derivatives of the present invention can be administered to animals, either orally or parenterally, in amounts sufficient to enhance the growth rate of the animal. Female ruminants are the preferred hosts for enhanced growth. The amount of allyl or propyl derivative administered to an animal varies, of course, with the animal, the desired rate of growth, and the like. The allyl or propyl derivative is frequently administered to ruminants in an amount of about 1 to 200, preferably about 1 to 50 milligrams per head per day.

The allyl or propyl materials herein can be administered in combination with a pharmaceutically-acceptable carrier. For example, the allyl or propyl compound can be employed as an additive in animal feed or as an implant under the skin. For example, the compounds can be blended with ordinary feed which contains nutritional values in an amount sufficient to produce the desired rate of growth, or the compounds can be suspended in a suitable injection suspension medium, such as peanut oil, and injected parenterally. From about 2.5 to 50 grams of the compound per ton of feed is typical. When an implant is used, for example a ball or cylindrical implant inserted under the skin on the ear of an animal, the implant will generally contain from about 1 mg. to 100 mg. of the compound. Other modes of parenteral administration include intramuscular, intravenous, and intraperitoneal injections.

When the allyl or propyl compounds herein are to be administered to animals in their feed, a feed composition may be prepared containing the usual nutritionally-balanced quantities of carbohydrates, proteins, vitamins, and minerals as diluents together with the compound. Some of the usual sources of these dietary elements are grains, such as ground grain and grain by-products; animal protein substances, such as those found in fish meal and meat scraps; vegetable proteins, such as soybean oil meal or peanut oil meal; vitaminaceous materials, e.g., mixture of vitamins A and D, riboflavin supplements and other vitamin B complex members; and bone meal and limestone to provide minerals. A type of conventional feed material for use with cattle, for example, includes alfalfa hay and ground corn cobs, together with supplementary vitaminaceous substances if desired.

The following examples involving allylzearalenones and propylzearalanone are offered to illustrate this invention; however, the invention is not limited to the specific materials, amounts, and procedures set forth. Melting points were taken on a Thomas-Hoover apparatus and are uncorrected. A Varian A 60-A instrument was used to record the $^1$H-NMR spectra in CDCl$_3$ with TMS as an internal standard.

EXAMPLE I

This example illustrates the preparation of 4-O-allylzearalenone, i.e. the compound of the formula:

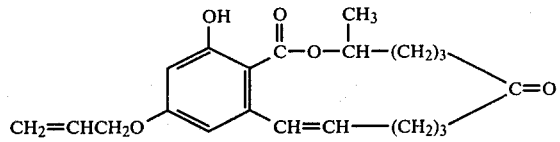

4-O-Allylzearalenone

Zearalenone (15.9 g, 0.05 mole), allyl bromide (24.2 g, 0.2 mole) and K$_2$CO$_3$ (10.0 g, 0.07 mole) were stirred and refluxed in acetone (200 ml) for 8 hours. The inorganic salts were removed by filtration and washed well with the solvent. The washings and the filtrate were combined and evaporated under reduced pressure. The residue was crystallized from 2-propanol to give 10 g of 4-O-allylzearalenone, mp 123°-125°. In the NMR Spectrum, a peak at δ 12.00 was indicative of the presence of chelated —OH proton at the 2-position; absence of a peak at ca. δ 8.00 of the —OH proton of the 4-position indicated allylation at this site. With the two aromatic protons at δ 6.38 and 6.48 (J=2.5 Hz), the rest of the spectrum was consistent with the assigned structure.

Anal.—Calc. for C$_{21}$H$_{26}$O$_5$: C,70.37; H,7.31; Found: C,70.63; H,7.13.

EXAMPLE II

This example illustrates the Claisen rearrangement preparation of 3-allylzearalenone, i.e. the compound of the formula:

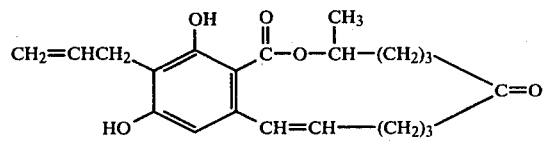

3-Allylzearalenone (Trans.)

4-O-Allylzearalenone as prepared in Example I (5.0 g) was placed in an oil bath maintained at 190°-195° for 5 hours. Thin Layer Chromatography (TLC) examination revealed only one principal product. The melt was chromatographed over a silica gel column (Baker #3404, 100 g, 28×3.3 cm) and eluted with C$_6$H$_6$ and CHCl$_3$ mixtures of increasing polarity. The fractions containing the product were evaporated together, and the product was crystallized from CH$_3$OH—H$_2$O to give 2.5 g of white crystals, mp 116°-118°. In the NMR spectrum, only one aromatic proton appeared as a singlet at δ 6.48 and the two peaks of phenolic proton resonances appeared at δ 12.00 and δ 8.64. The C-1' olefinic proton appeared as a doublet at δ 7.12 (J=15 Hz).

Anal.—Calc. for $C_{21}H_{26}O_5$: C,70.37; H,7.31. Found: C,70.47; H,7.33.

EXAMPLE III

This example illustrates the preparation of 3-allyl-cis-zearalenone, i.e., the compound of the formula:

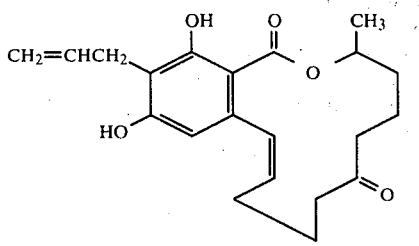

3-Allyl-cis-zearalenone

The 3-allylzearalenone as prepared in Example II (1.3 g) was photoisomerized to its cis-stereoisomer in $CH_3OH$ (100 ml) for 60 hours according to the method disclosed in Peters, *J. Med Chem.*, 15, p. 867 (1972). Evaporation gave a glassy substance (1.2 g) which could not be purified by crystallization. The NMR spectrum indicated 90–95% conversion. The doublet resonance of the C-1' olefinic proton appeared at δ 6.65 (J=12 Hz) and the singlet resonance of the aromatic proton appeared at δ 6.26.

EXAMPLE IV

This example illustrates the preparation of 3-(1-propyl)-zearalanone, i.e., the compound of the formula:

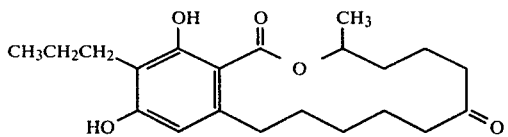

3-(1-Propyl)zearalanone

The 3-allylzearalenone is prepared in Example II (1.0 g) was hydrogenated at 50 lbs pressure in $CH_3OH$ (100 ml) for 3 hours in the presence of Pd/C (5%, 0.1 g). The catalyst was removed via filtration, the filtrate was evaporated under reduced pressure, and the residue was crystallized from $CH_3OH-H_2O$ to yield 1.1 g of white crystals, m.p. 161°–162.5°. The NMR spectrum was consistent with the assigned structure.

Anal.—Calc for $C_{21}H_{30}O_5$: C,69.58; H,8.34. Found: C,69.70; H,8.40.

EXAMPLE V

This example illustrates the use of 4-O-allylzearalenone as a growth promoting supplement in animal feed.

For young beef cattle, i.e., calves to yearlings running to two year olds, each animal is given 5 to 20 milligrams per day of 4-O-allylzearalenone intimately admixed in about 18 to 22 pounds per head per day of a complete pelleted ration for about 180 days. The complete pelleted ration includes, in addition to 4-O-allylzearalenone, the following:

| Barley | weight percent: | 40–43 |
|---|---|---|
| Molasses dried beet pulp | weight percent: | 34.5–37.5 |
| Alfalfa pellets | weight percent: | 8.0 |
| Tallow | weight percent: | 2.5 |
| Calcium carbonate | weight percent: | .30 |
| Urea | weight percent: | .30 |
| Phosphorus source | weight percent: | .40 |
| Salt | weight percent: | .50 |
| Molasses | weight percent: | 10.00 |
| Trace mineral | weight percent: | 0.5 |
| Vitamin A | MMI.U/ton: | 2–4 |

Note: Milo or corn, for example, can be substituted for the barley.

The 4-O-allylzearalenone is admixed with the above ingredients in a stationary blender or a feed mix truck in the following amount in grams per ton to provide an appropriate complete pelleted feed with dosage levels ranging from 5 to 90 milligrams per head per day.

| Grams/ton: | Mg/head/day |
|---|---|
| 0.5 | 5 |
| 1.0 | 10 |
| 2.0 | 20 |
| 4.0 | 40 |
| 8.0 | 80 |

These gram amounts are premixed with, for example, 10 pounds of soybean hulls prior to admixture with the other ingredients.

EXAMPLE VI

This example illustrates the use of 3-allylzearalenone as a growth promoting supplement in animal feed.

For young swine, i.e., six week old pigs to about 100 pound pigs, each animal is given 5 to 2 milligrams per day of 3-allylzearalenone intimately admixed in about 1½ to 5½ pounds per head per day of a grower ration until it reaches a weight of about 100 pounds. When the swine weigh between 90 and 125 pounds, the feed is changed to one whereby each animal is given 20 to 50 milligrams per day of the compound intimately admixed in about 5½ to 10 pounds per head per day of a finisher ration until it reaches market weight of about 220 pounds. The grower and finisher ration include, in addition to the 3-allylzearalenone, the following:

| Ingredients | Grower, wt. percent | Finisher, wt. percent |
|---|---|---|
| Ground Yellow Corn | 77 | 86.7 |
| Soybean Meal (44% protein) | 16 | 6.5 |
| Meat and Bone Scraps (50% protein) | 2.5 | 2.5 |
| Dehydrate Alfalfa Meal (17%) | 2.5 | 2.5 |
| Steamed Bone Meal | 0.5 | 0.5 |
| Ground Limestone | 0.5 | 0.3 |
| Iodized Salt | 0.5 | 0.5 |
| Vitamin, Antibiotic and Trace Mineral Premix | 0.5 | 0.5 |

The 3-allylzearalenone is admixed with the above ingredients in a blender in the following amounts in milligrams per pound to provide an appropriate feed with dosage levels ranging from 6 to 96 milligrams per head per day.

| Mg/pound: | Mg/head/day |
|---|---|
| 2 | 6 |
| 4 | 12 |
| 8 | 24 |
| 16 | 48 |

| Mg/pound: | Mg/head/day |
|---|---|
| 32 | 96 |

Substantially similar growth promoting feed compositions are realized when, in the Example VI feed compositions, the 3-allylzearalenone is replaced with an equivalent amount of 3-(1-propyl)zearalanone.

What is claimed is:
1. 4-O-Allylzearalenone.
2. 3-Allylzearalenone.
3. 3-Allyl-cis-zearalenone.
4. 3-(1-Propyl)zearalanone.
5. A feed for animals comprising a nutritional diluent and a growth-promoting amount of a compound of claim 1, 2, 3 or 4.
6. An animal growth-promoting composition comprising a pharmaceutically acceptable carrier and a growth-enhancing amount of a compound of claim 1, 2, 3 or 4.
7. A method for producing a growth-promoting effect in an animal comprises administering to the animal a sufficient amount of a compound of claim 1, 2, 3 or 4 to promote the growth of the animal.

* * * * *